(12) United States Patent
Ekenberg (10) Patent No.: US 6,218,531 B1
(45) Date of Patent: Apr. 17, 2001

(54) METHOD OF ISOLATING RNA

(75) Inventor: Steven J. Ekenberg, Mount Horeb, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/445,944

(22) PCT Filed: Jun. 25, 1998

(86) PCT No.: PCT/US98/13180

§ 371 Date: Dec. 20, 1999

§ 102(e) Date: Dec. 20, 1999

(87) PCT Pub. No.: WO98/59076

PCT Pub. Date: Dec. 30, 1998

Related U.S. Application Data (60) Provisional application No. 60/050,719, filed on Jun. 25, 1997.

(51) Int. Cl.$^7$ .............................. C07H 21/04; C12Q 1/68; C12P 19/34; B01D 15/08
(52) U.S. Cl. .................... 536/25.41; 435/6; 435/91.1; 435/91.2; 536/25.4; 536/25.42; 536/25.32; 536/23.1; 210/656
(58) Field of Search .................. 435/6, 91.1, 91.2; 536/23.1, 25.4, 25.41, 25.42, 25.32; 210/656

(56) References Cited

U.S. PATENT DOCUMENTS

| | | |
|---|---|---|
| 5,075,430 | 12/1991 | Little et al. . |
| 5,155,018 | 10/1992 | Gillespie et al. . |
| 5,459,253 * | 10/1995 | Wolin et al. ................. 536/25.42 |
| 5,658,548 | 8/1997 | Padhye et al. . |

FOREIGN PATENT DOCUMENTS

| | | |
|---|---|---|
| WO 95/34569 | 12/1995 | (WO) . |
| WO 96/08500A1 | 3/1996 | (WO) . |

OTHER PUBLICATIONS

Sambrook, et al. Molecular Cloning A Laboratory Manual, Second edition. Cold Spring Harbor Press, 1989, vol. 1, p. 7.3 et seq.

Inglis, P.W. et al. Rapid Isolation of Double–stranded RNAs From Entomopathogenic Species . . . J. of Virol. Meth. 1997, vol. 67, pp 113–116.

Boom, R. et al. Rapid and Simple Method for Purification of Nucleic Acids, J. of Clin. Microbiol. Mar. 1990, vol. 28, No. 3, pp 485–503.

Chirgwin, J.M. et al Isolation of Biologically Active Ribonucleic Acid from Source Enriched in Ribonuclease. Biochemistry. 1979, vol. 18, No. 24, pp 5294–5299.

Vogelstein, B. et al. Preparative and Analytical Purification of DNA from Agarose. Proc. Natl. Acad. Sci., USA. Feb. 1979, vol. 76, No. 2, pp 615–619.

Ausubel, F. et al. Current Protocols in Molecular Biology, Wiley–Interscience New York (1993) Ch. 2 (DNA) and Ch. 4 (RNA).

Marko et al. Anal. Biochem. 121, 382–387 (1982).

Chen and Thomas Anal. Biochem. 101, 339–341 (1980).

Wizard (TM) Plus SV DNA, Promega Corporation (No Date).

High Pure RNA Isolation Kit (Catolog No. 1828 665), product insert, Boehringer–Mannheim GmbH (Mannheim, Germany) (No Date).

RNeasy (TM) Total RNA Kit from Qiagen, Inc. Dec. 1994 (Chatsworth, California, U.S.A.).

Protocols and Applications Guide, Promega Corporation, 3rd ed. p. 93 et seq (1996).

RNAgents Total RNA Isolation System, 1996 Promega Product Catalogue, p. 174.

\* cited by examiner

Primary Examiner—Kenneth R. Horlick
Assistant Examiner—Jeffrey Siew
(74) Attorney, Agent, or Firm—Michael Best & Friedrich LLP; Grady J. Frenchick; Karen B. King (57) ABSTRACT

The present invention provides a method for isolating RNA from a biological material comprising RNA and contaminants, wherein: the biological material is disrupted in the presence of a chaotropic agent, the resulting lysate is diluted to precipitate out contaminants, and the precipitate is removed from the lysate. RNA is preferably isolated from the resulting cleared lysate, using a silica matrix to bind and then release RNA bound thereto under particular conditions. The present invention also provides a method for isolating RNA from a solution comprising RNA and DNA, wherein: the RNA and DNA are bound to a silica matrix in the presence of at least one binding enhancer, the DNA is digested with DNase, and the RNA fluted therefrom.

16 Claims, 3 Drawing Sheets

METHOD OF ISOLATING RNA

CROSS-REFERENCE TO RELATED APPLICATIONS

This Appln is a 371 of PCT/US98/13180 filed Jun. 25, 1998 and also claims the benefit of Provisional No. 60/050,719 filed Jun. 25, 1997.

BACKGROUND OF THE INVENTION

This invention relates to the field of materials and methods for isolating biological entities, specifically, to materials and methods for isolating nucleic acids such as ribonucleic acid (RNA) or deoxyribonucleic acid (DNA) from other material in a biological sample, such as cellular debris. More specifically, and without intending to limit the scope hereof, this invention particularly relates to the field of materials and methods for isolating RNA, more particularly to materials and methods for isolating total RNA from biological material such as animal or plant tissue, cultured tissue culture cells, yeast, bacteria, blood cells, viruses, or serum.

Many molecular biological techniques such as reverse transcription, cloning, restriction analysis, and sequencing involve the processing or analysis of biological materials. These techniques generally require that such materials be substantially free of contaminants capable of interfering with such processing or analysis procedures. Such contaminants generally include substances that block or inhibit chemical reactions, (e.g. nucleic acid or protein hybridizations, enzymatically catalyzed reactions, and other types of reactions, used in molecular biological techniques), substances that catalyze the degradation or de-polymerization of a nucleic acid or other biological material of interest, or substances that provide "background" indicative of the presence in a sample of a quantity of a biological target material of interest when the nucleic acid is not, in fact, present in the sample. Contaminants also include macromolecular substances from the in vivo or in vitro medium from which a nucleic acid material of interest is isolated, macromolecular substances such as enzymes, other types of proteins, polysaccharides, or polynucleotides, as well as lower molecular weight substances, such as lipids, low molecular weight enzyme inhibitors, or oligonucleotides. Contaminants can also be introduced into a target biological material from chemicals or other materials used to isolate the material from other substances. Common contaminants of this last type include trace metals, dyes, and organic solvents.

Obtaining nucleic acids, such as RNA or DNA, which are sufficiently free of contaminants for molecular biological applications is complicated by the complex systems in which the nucleic acids are typically found. These systems, e.g., cells from tissues, cells from body fluids such as blood, lymph, milk, urine, feces, semen, or the like, cells in culture, agarose or polyacrylamide gels, or solutions in which target nucleic acid amplification has been carried out, typically include significant quantities of contaminants from which the DNA or RNA of interest must be isolated before being used in a molecular biological technique.

Many different methods have been employed over the past several years to isolate target nucleic acids, such as DNA or RNA or specific types of DNA or RNA, from various different types of biological material. See, e.g. Chapter 2 (DNA) and Chapter 4 (RNA) of F. Ausubel et al., eds., *Current Protocols in Molecular Biology,* Wiley-Interscience, New York (1993). Conventional nucleic acid isolation protocols begin with the disruption of a sample of biological material under conditions designed to cause any target nucleic acid contained therein to be released into the disruption solution. Cells with a lipid bilayer membrane, such as bacteria cells, eukaryotic tissue culture cells, or blood cells are generally disrupted by being suspended in a solution and by adding a lysis buffer containing enzymes and/or chemicals designed to lyse the cells gently and to release the target nucleic acid into the solution. When RNA is the target nucleic acid to be isolated, biological material disruption is conventionally done under conditions designed to inhibit enzymes such as ribonucleases (RNases) capable of degrading RNA. One conventional way of inhibiting RNases during cell lysis and the initial processing steps is to include a guanidine salt, such as guanidine thiocyanate, and β-mercaptoethanol in the disruption solution. Chirgwin (2979) *Biochemistry* 18:5294. Once the biological material is sufficiently disrupted to release the target nucleic acid material into the disruption solution, the resulting solution is generally spun in a centrifuge to remove at least some of the cell debris and any precipitates formed in the disruption solution during the disruption step. The supernatant is then decanted and processed further to separate the target nucleic acid material from other contaminants in the solution.

Conventional nucleic acid isolation protocols also generally use phenol or an organic solvent mixture containing phenol and chloroform to extract cellular material, such as proteins and lipids, remaining in the disruption solution supernatant produced as described above The phenol/chloroform extraction step is followed by precipitation of the nucleic acid material remaining in the extracted aqueous phase by adding alcohol, such as ethanol or isopropanol, to that aqueous phase. The precipitate is typically removed from the solution by centrifugation, and the resulting pellet of precipitate is allowed to dry before being resuspended in water or a buffer solution for further processing or analysis. The alcohol precipitation step serves two purposes in a conventional nucleic acid isolation procedure. Specifically, it allows one further to isolate the nucleic acid material from contaminants including residual phenol or chloroform remaining in the organic phase, and it allows one to resuspend the resulting precipitated nucleic acid in any solution for any final desired nucleic acid concentration. For examples of conventional lysis and organic extraction methods for isolating total RNA from various types of biological material, see: *Molecular Cloning* by Sambrook et al., 2nd edition, Cold Spring Harbor Laboratory Press, p. 7.3 et seq (1989); *Protocols and Applications Guide* produced by Promega Corporation, 3rd edition, p. 93 et seq. (1996); and by Chirgwin, J. M. et al, 18 *Biochemistry* 5294 (1979); all of which are incorporated by reference herein. Several different companies, including Promega Corporation (Madison, Wis., USA), have also developed kits which include reagents designed to be used in isolating RNA or mRNA from biological material using such methods of isolation. See, e.g. the RNAgents® Total RNA Isolation Systems and the PolyATract® Systems available from Promega and described in the 1996 Promega Product Catalogue at page 174.

Conventional nucleic acid isolation procedures have significant drawbacks. Among these drawbacks are the time required for the multiple extraction steps needed to isolate any given nucleic acid material from other materials present in a solution produced from disrupting a biological material. For example, multiple extraction steps are required to isolate RNA from proteins, lipids, and chromosomal DNA, all of which are present in a solution produced from disrupting tissue culture cells or plant or animal tissue. Another drawback of conventional nucleic and isolated procedures is the need to use phenol and chloroform. Phenol is a known carcinogen, which causes severe burns on contact with skin. Chloroform is highly volatile, toxic and flammable. Another undesirable characteristic of organic extractions with phenol is that the oxidation products of phenol can damage nucleic acids. Only freshly redistilled phenol can be used, and nucleic acids cannot be left in the presence of phenol. Finally, some of the nucleic acid material is inherently lost at each organic extraction step as well as in the alcohol precipitation stage. Consequently, even under the best circumstances such conventional methods are time consuming, hazardous, and produce relatively low yields of isolated nucleic acid material. Also, the resulting isolated nucleic acid material is frequently contaminated with impurities, particularly with organic solvents, alcohol, and/or non-target nucleic acid material (e.g. chromosomal DNA contaminant from an RNA isolation procedure).

When a target nucleic acid of a particular molecular weight or size is required for additional analysis, molecular biologists frequently use polyacrylamide or agarose gel electrophoresis to fractionate total RNA or DNA or mixtures of RNA and DNA isolated according to one of the conventional procedures described above. The DNA or RNA is sometimes processed prior to fractionation by electrophoresis using conventional methods to produce RNA or DNA of the desired size or which includes a particular sequence of interest, e.g. by using the polymerase chain reaction (PCR), reverse transcriptase PCR (RT-PCR), or linker attachment. For analysis or treatment by a molecular biological procedure after fractionation, the RNA or DNA of interest in the fraction(s) must be separated from contaminants, such as agarose, other polysaccharides, polyacrylamide, acrylamide, or acrylic acid, in the gel used in such electrophoresis. Conventional procedures similar to those used to isolate total RNA or DNA as described above have also been developed to isolate nucleic acid material from such contaminants in electrophoresis gels. For example, when the nucleic acid material of a desired molecular weight is fractionated on an agarose gel, the band on the gel containing the desired material can be cut out of the gel and processed as follows. The excised band is then processed by digesting the agarose in the bank using an Agarase enzyme, or processed by removing the nucleic acid material from the excised band of gel material by electroelution. Whether digestion or electroelution is used to separate the nucleic acid material of interest from the gel, the nucleic acid material is conventionally isolated further using multiple organic extraction steps using phenol and chloroform, as described above, followed by alcohol precipitation used to isolate the resulting nucleic acid material from the agarose or other contaminates in the gel. Such conventional fractionation, digestion, and isolation procedures are very time consuming and suffer from the same disadvantages of low yield and impurities from organic and alcohol contaminants as are common in the conventional general nucleic acid isolation methods described above.

Silica based nucleic acid isolation techniques have been developed as alternatives to, or in addition to, the conventional isolation techniques described above. In these alternative techniques, silica materials, such as glass particles, glass powder, silica particles, glass microfibers, diatomaceous earth, and mixtures of the above have been employed in combination with aqueous solutions of chaotropic salts to isolate DNA, particularly plasmid DNA. See U.S. Pat. No. 5,075,430 and references cited therein, including Marko et al., *Anal. Biochem.* 121, 382–387 (1982) and Vogelstein et al., *Proc. Natl. Acad. Sci.* (USA) 76, 615–619 (1979). See also Boom et al., *J. Clin. Microbiol.* 28, 495–503 (1990). With reference to intact glass fiber filters used in combination with aqueous solutions of a chaotropic salt to separate DNA from other substances, see Chen and Thomas, *Anal. Biochem.* 101, 339–341 (1980). Numerous commercial sources offer silica-based matrices designed for use in isolating DNA using either centrifugation or vacuum filtration. See, e.g. Wizard™ Plus SV DNA purification systems line of products from Promega Corporation; or the QiaPrep™ line of DNA isolation systems from Qiagen Corp. (Chatsworth, Calif., U.S.A.).

Silica-based systems and methods have also been developed in recent years for use in isolating total RNA from at least some types of biological materials. For example, one company has developed an RNA isolation kit wich uses a glass fiber filter in a spin filter basket and a hybrid lysis buffer/binding solution with a high concentration of guanidine hydrochloride, a choatropic agent, to isolate total RNA from simple biological materials, such as cultured cells, blood, yeast, and bacteria. See, e.g. Product Insert for the High Pure RNA Isolation Kit (Catalog Number 1828 665) from Boehringer-Mannheim GmbH (Mannheim, Germany). Another company has developed a system for isolating total RNA from bacteria cells and tissue using a spin basket with a silica gel-based membrane, and a lysis buffer/binding solution containing guanidinium isothiocyanate. See, e.g. the RNeasy™ Total RNA Kit from QIAGEN Inc. (Chatsworth, Calif., U.S.A.), as described in the December 1994 RNeasy™ Handbook from QIAGEN. Both commercial systems described briefly above allow one to isolate total RNA quickly, but the yield and purity of RNA isolated thereby tends to be low, particularly when used to isolate RNA from complex biological materials, such as plant or animal tissue.

Known silica-based RNA isolation techniques employ the same basic sequence of steps to isolate target RNA from any given biological material. However, the concentrations and amounts of the various solutions used in each such procedure vary depending upon the composition of the silica-based matrix used in the method. The basic sequence of steps used in all known silica-based RNA isolation process consists of disruption of the biological material in the presence of a lysis buffer, followed by formation of a complex of nucleic acid(s) and a silica matrix, followed by removal of the lysis buffer mixture from the resulting complex and washing of the complex, followed by elution of the target nucleic acid from the complex. The steps of the basic known silica-based RNA isolation techniques are reviewed in greater detail below, with particular emphasis on the materials and methods used to isolate total RNA from biological material using the two commercial silica-based RNA isolation kits cited above, according to the manufacturer's instructions.

A chaotropic salt is included in the lysis buffer used in the first, disruption, step of the silica-based RNA isolation techniques to protect the RNA formerly contained in the biological material from enzymatic degradation during and after disruption. The species and amount of chaotropic salt in the lysis buffer is chosen to promote binding of the RNA in the resulting lysate to whatever form of silica matrix is used in the next step of the technique. For example, a lysis/binding buffer containing guanidine hydrochloride, a chaotropic salt, and a Triton® X-100 (a non-ionic detergent) is provided for use in disrupting biological material and promoting binding to the silica matrix in the spin columns sold with the High Pure RNA Isolation Kit (Boehringer Mannheim GmbH). The lysis/binding buffer provided with the RNeasy™ Total RNA Kit (QIAGEN Inc.) for use in the same basic disruption step contains guanidinium isothiocyanate, a similar chaotropic salt.

Disruption of a sample of biological material is followed immediately by centrifugation to remove particulate cell debris from the lysate. The High Pure RNA Isolation Kit is a exception to this general rule, and calls for proceeding immediately from lysis to application of the crude lysate to the spin column provided with that kit. For methods of isolation, including the method used with the RNeasy™ Total RNA Kit, which do include the preprocessing step of centrifugation of a crude lysate prior to contact with a silica matrix, the amount of cell debris typically removed in the preprocessing step is generally very low, particularly in comparison to the amount of impurities inherently present in a lysate solution. Many of the impurities remaining in the solution, particularly protein, lipid, and chromosomal DNA can clog the silica matrix and compete with binding of RNA species to the matrix in the next step of the method. Some of those impurities, particularly proteins and chromosomal DNA can also co-elute from the matrix with RNA in the final elution step of the method, below. Lysis of complex biological materials, such as animal or plant tissue, releases a large number of contaminants in to the lysis solution in the first step of the general silica based RNA isolation procedure described above. The higher the concentration of contaminants in the lysate solution, the more likely the contaminants will clog the silica matrix. Some silica based matrices are so sensitive to clogging that they cannot be used to process complex biological material, regardless of whether one pre-clarifies the lysate solution by centrifugation. See, e.g. High Pure RNA Isolation Kit from Boehringer Mannheim, which only comes with instructions for use in isolating RNA from cultured cells, blood, yeast, and bacteria, and which tends to clog to the point of being unusable when used to isolate RNA from more complex tissue.

The silica matrix used to isolate RNA in such procedures is generally in the form of silica material impregnating or coating a filter, in the form of a resin, or in the form of magnetic beads coated with silica. Regardless of the form in which it occurs, the silica matrix in the general procedure described above is placed in a filter basket, before or after being bound to nucleic acid materials in the lysate solution. The filter basket is typically shaped like a hollow tube, with an open inlet end and a closed base end. The filter basket contains at least one filter fitted into the inside of the basket at its base end, and the base has openings which allow solutions passing through the filter to flow out of the basket through the openings. The filter fitted into the base of the basket is designed to retain the silica material in the basket, and to permit solutions of disrupted biological material to pass through the filter into the collection tube when the basket is subjected to an external force, such as centrifugation or a vacuum.

Commercial filter baskets are typically designed to fit into a standard sized microcentrifuge collection tube in such a way that the basket/tube assembly fit inside a standard microcentrifuge. Some filter baskets are also designed to fit into a collection tube as well as being designed to form a substantially air tight seal with a vacuum manifold, either directly through an adapter which is a part of the base of the filter basket, or indirectly by fitting into a separate vacuum manifold adapter. For an example of this last type of filter basket and separate manifold adapter assembly, see the Wizard® Plus SV Minipreps Spin Columns and manifold adapters from Promega Corp. For an example of filter basket assemblies designed to be used only with spin filtration, see the spin columns provided with the two commercial RNA isolation kits described above, i.e. the RNeasy™ Total RNA Kit (QIAGEN, Inc.) and the High Pure RNA Isolation Kit (Boehringer Mannheim GmbH).

In the next stage of known silica-based RNA isolation methods, the lysate solution is placed into contact with a silica matrix in the presence of a sufficiently high concentration of a chaotropic salt to promote the binding of RNA with the silica matrix. Known silica-based RNA isolation procedures, including both commercial procedures described above, include a sufficient amount of chaotropic salt to promote binding to the silica matrix in the lysate solution created in the first step of the procedure. Once placed in contact with the silica matrix, the lysate solution is removed therefrom, using external force, such as centrifugation or vacuum filtration. As noted above, this solution removal process can be difficult when the concentration of contaminants in the lysate solution placed in contact with the matrix is high, such as are generally present in lysates of complex biological materials.

Once the lysate solution is removed from the silica matrix, the matrix is washed in a series of wash steps, involving applying a wash solution to the matrix and removing it therefrom.

The High Pure RNA Isolation Kit (Boehringer Mannheim GmbH) includes reagents designed to treat the silica matrix after removal of the lysate solution as described above, before beginning the wash steps of that procedure. Specifically, the High Pure RNA Isolation Kit includes lyophilized DNase I and a DNase incubation buffer consisting of 1 M NaCl, 20 mM Tris-HCl and 10 mM $MnCl_2$, pH 7.0 (25° C.). The kit instructions call for suspending the lyophilized DNase in water, and adding the suspended DNase and incubation buffer directly to the silica matrix, the glass fiber filter in the base of the spin filter basket provided with that kit, and allowing the solution to incubate in contact with the filter for 15 minutes. A first wash buffer containing guanidine hydrochloride and ethanol is then added to the filter basket, and removed by centrifugation. That first wash step is then followed by a second and third wash step with a second wash solution which contains only a buffer, salt (not a chaotropic salt) and ethanol.

The DNase treatment step in the High Pure RNA Isolation Kit procedure uses a high concentration sodium chloride salt solution. Unfortunately, DNase I is considerably less active in such high salt solutions, and therefore more enzyme must be added to digest the same amount of DNA compared to what would be required in a lower salt buffer. By adding larger amounts of DNase to the silica matrix, one increases the number of contaminants which must be removed from the matrix before the final elution step.

Once the wash steps in a silica based isolation procedure are complete, the RNA is eluted from the silica matrix using an elution buffer, usually a low salt buffer or water. The buffer is applied to the matrix, and then removed from the matrix into a sterile collection tube by centrifugation. Unfortunately, protein and other contaminants tend to co-elute from the two commercial silica matrices when used to isolate RNA according to the manufacturers' instructions provided with the two commercial RNA isolation kits described above. Also, the yield of RNA isolated using High Pure Isolation Kit spin columns tends to be low compared to yields obtained using other techniques and systems. RNA eluted from the RNeasy™ Total RNA Kit spin columns tends to be contaminated with chromosomal DNA. See Example 6 and FIG. 3, below, for test results illustrating the chromosomal contamination problem with this particular kit and associated method of isolation.

What is needed is a method or methods for isolating RNA from a sample of biological material, whereby the RNA isolated thereby is substantially free of contaminants, including proteins, lipids, genomic DNA, and any chemicals likely to inhibit or interfere with processing or analysis of the isolated RNA. The present invention provides methods for isolating RNA which is substantially free of such contaminants, using the types of silica matrices and filter basket assemblies and general isolation techniques described above. The RNA isolation method of the present invention produces a high yield of RNA, and is less labor intensive than conventional RNA isolation techniques. The RNA isolated in a practice of the method of the present invention is particularly well suited to such contamination sensitive subsequent molecular biology applications as cDNA library construction, reverse transcriptase polymerase chain reaction (RT-PCR), and as a substrate in various other forms of analysis. Many other applications of RNA separated or isolated using the present invention will be apparent to one skilled in the art.

BRIEF SUMMARY OF THE INVENTION

Briefly, in one aspect, the present invention is a method of isolating RNA from a sample of biological material, comprising the steps of:

a) providing a biological material comprising RNA and contaminants, wherein the contaminants include DNA and proteins;

b) disrupting the biological material in a first container in the presence of a lysis buffer containing at a chaotropic salt, thereby producing a lysate solution and cell debris, wherein the concentration of chaotropic salt in the lysis buffer is at least about 0.5 molar;

c) adding a sufficient volume of a dilution buffer to the lysate solution to form a precipitate of the contaminants in the lysate solution; and d) removing the precipitate from the diluted lysate solution, thereby forming a cleared lysate solution.

In a preferred aspect of the method of isolating RNA of the present invention, a silica matrix is used to further isolate RNA from other contaminants in the cleared lysate solution formed in step (d) of the method, above. This preferred aspect of the method further comprises the steps of:

e) providing a silica matrix with a capacity to bind RNA;

f) adding a reagent mixture to the cleared lysate solution, thereby forming a binding mixture, wherein the binding mixture is configured to promote binding of the RNA to the silica matrix;

g) placing the binding mixture in contact with the silica matrix, wherein the RNA forms a complex with the silica matrix;

h) removing the binding mixture from the complex;

i) washing the complex by adding at least one wash solution to the complex and removing it therefrom;

j) eluting the RNA from the complex by placing the complex into contact with an elution buffer, thereby promoting release of the RNA from the complex into the elution buffer; and k) removing the elution buffer containing the eluted RNA from the complex.

In another preferred aspect of the method described immediately above, when the binding mixture added to the silica matrix in step (g) contains DNA, and the complex formed by adding the binding mixture to the silica matrix in step (g) comprises a complex of RNA, DNA, and the silica matrix, the DNA is preferably removed from the complex by digestion with DNase before the RNA is eluted from the complex in step (j). DNase digestion of the complex of RNA, DNA, and the silica matrix is preferably done according to the additional processing steps comprising:

placing the complex in contact with DNase in the presence of a DNase incubation buffer;

incubating the DNase and complex mixture for at least one minute to allow the DNase to digest the DNA;

adding a chaotropic salt mixture to the complex at the end of the incubation period, wherein the chaotropic salt mixture comprises a sufficient amount of a chaotropic salt to inactivate the DNase and to promote retention of RNA in the complex;

removing the chaotropic salt mixture from the complex; and washing the complex again according to washing step (j).

In an alternative aspect, the method of isolating RNA of the present method comprises the steps of:

a) providing a binding mixture comprising RNA, DNA, and a binding enhancer, wherein the binding enhancer is selected from the group consisting of a non-chaotropic salt, an alcohol, and a chaotropic salt;

b) placing the resulting binding mixture in contact with the silica matrix, wherein the RNA and the DNA form a complex with the silica matrix;

c) washing the silica matrix by adding a wash buffer to the matrix and removing the wash buffer therefrom;

d) adding DNase and an DNase incubation buffer to the complex;

e) incubating the resulting mixture of DNase, incubation buffer, and complex for an incubation period of at least one minute, wherein the DNase digests the DNA;

f) inactivating the DNase and enhancing binding of RNA to the silica matrix in the DNase treated complex by adding a chaotropic salt mixture to the complex at the end of the incubation period, wherein the chaotropic salt mixture comprises a chaotropic salt;

g) removing the resulting second binding mixture from the complex;

h) washing the matrix by adding a second wash buffer to the complex and removing the wash buffer therefrom; and i) eluting the RNA from the matrix by adding an elution buffer to the complex and removing it therefrom to an RNase-free container, wherein the composition of the elution buffer used to elute the RNA is designed to promote the release of RNA from the matrix.

Any silica-based matrix capable of reversibly binding RNA can be used in the method of the present invention. However, the silica matrix is preferably incorporated into or bound to the surface of at least one filter disk in the base of a filter basket. The filter basket used in practicing the methods of isolating RNA of the present invention is preferably designed to fit into a centrifuge tube, so one or more of the solutions used in the present methods can be removed from the filter basket using centrifugation. The filter basket used in the methods of the present invention is more preferably additionally designed to fit into a vacuum manifold adapter, so one can have the option of using vacuum filtration to remove one or more of the solutions used in the present methods from the filter basket. The most preferred filter baskets and assemblies used in the methods of the present invention are the filter baskets and assemblies described as the most preferred for nucleic acid isolation methods, in general, in U.S. provisional patent application Ser. No. 60/026,582, filed Sep. 18, 1996, incorporated herein by reference. One particularly preferred embodiment of the filter baskets and assemblies disclosed therein was introduced into the market after that provisional application was filed, a filtration assembly sold with a DNA isolation system under the brand name, Wizard® Plus SV Minipreps DNA Purification System, an assembly provided with vacuum adapters designed to interfit with the Vac-Man Jr.® laboratory manifold, both of which are sold by Promega Corp.

The methods of the present invention are designed to isolate substantially intact RNA in a relatively short period of time, preferably in less than an hour, more preferably in less than thirty minutes, and most preferably in less than twenty minutes. The term "substantially intact" is used herein to mean RNA which is not visibly degraded compared to an intact RNA control sample run out on a standard nucleic acid gel electrophoresis analysis gel stained with ethidium bromide or any other chemical known to stain nucleic acid material in such a gel.

RNA isolated according to the most preferred aspects of the methods of the present invention is also substantially free of contaminants, including DNA, proteins, and chaotropic salts. The term "substantially free of contaminants" is used herein to mean RNA which does not contain detectable amounts of any such contaminants, when analyzed spectrophotometrically and by gel electrophoresis, and which is usable in functional assays known to be sensitive to contaminants. The isolated RNA is substantially free of contaminating proteins and chaotropic salts if neither contaminant is present in amounts which can be detected using standard spectrophotometric analysis techniques. The isolated RNA is also substantially free of contaminants if it can be used in a sensitive functional assay, such as used as a template in a reverse transcriptase polymerase chain reaction (RT-PCR). The isolated RNA is substantially free of contaminating chromosomal DNA if no chromosomal DNA bands can be detected by fractionating the products of amplifying isolated RNA with RT-PCR using gel electrophoresis, and by detecting nucleic acids in the resulting gel using standard staining or other detection techniques.

As is further demonstrated in the detailed description and examples below, the present method of isolating RNA provides a fast, efficient, useful means for producing large yields of substantially intact RNA substantially free of contaminants.

DETAILED DESCRIPTION OF THE INVENTION

The methods of the present invention can be used to isolate RNA from any one of a number of different sources, including biological material such as cells or tissue, bands extracted from electrophoresis gels, RNA polymerization reactions, or partially purified RNA solutions. The description of the present method, below, is directed to the isolation of RNA from biological material, as such material is the most difficult of all of the sources described above from which to isolate intact, functional RNA. This description is not, however, intended to limit the scope of the present invention to the isolation of RNA from such sources alone, as the present method can also be used to isolate RNA from other sources, such as run-off transcription reactions or solutions of partially isolated RNA obtained using methods other than those described below.

The method of the present invention uses chaotropic salts in several different ways. First, such agents are present at the lysis stage to ensure the biological material is sufficiently disrupted to release RNA contained therein into the lysis solution, and to inactivate enzymes likely to degrade the RNA, particularly RNases. Such agents, in association with detergents, such as sodium lauryl sulphate (SDS), also serve to disrupt nucleo-protein interactions, thereby further releasing the RNA in solution and inactivating any degradative enzymes such as RNases in solution which might otherwise degrade any RNA present therein. Chaotropic salts are also among the binding enhancers one can select to include in the binding mixture placed in contact with a silica matrix to form a complex of the RNA and the silica matrix in the further processing steps of some of the aspects of the methods of the present invention. A chaotropic salt is also included in the chaotropic salt mixture added to the DNase mixture after incubation of a complex of RNA, DNA, and silica matrix with DNase, in some of the preferred forms of the method of isolating RNA of the present invention. The chaotropic salt in the chaotropic salt mixture inhibits further DNase activity and promotes restoration of the RNA and silica matrix complex prior to further processing steps.

Chaotropic salts are only one of at least three different types of binding enhancers suitable for use in the reagent mixtures of the present invention. Other binding enhancers include non-chaotropic salts (e.g. sodium, calcium, lithium, or potassium salts, preferably a chloride salt of at least one of the above) and ethanol. When only one binding enhancer is used, the concentration of enhancer in the mixture needed to promote formation of the RNA silica matrix complex is high compared to the concentration needed when two or more enhancers are included in the mixture. When only one binding enhancer is used the enhancer is preferably at least 30% by weight of ethanol, or at least 0.4M of a non-chaotropic salt such as sodium chloride, or at least one molar of a chaotropic salt such as guanidine thiocyanate is needed to promote complex formation. However, formation of the complex occurs in the presence of considerably smaller concentrations of combinations of two or more of these same three binding enhancers. The most preferred binding mixture contains both ethanol and a chaotropic salt. When DNA is present in the binding mixture along with RNA, the composition of binding enhancers in the mixture is preferably optimized to favor the formation of an RNA silica matrix complex over the formation of a DNA silica matrix complex.

Chaotropic salts are salts of chaotropic ions. Such salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, to melt (i.e., strand-separate). It is thought that chaotropic ions have these effects because they disrupt hydrogen-bonding networks that exists in liquid water and thereby make denatured proteins and nucleic acids thermodynamically more stable than their correctly folded or structured counterparts. Chaotropic ions include guanidinium, iodide, perchlorate and trichloroacetate. Preferred in the present invention is the guanidinium ion. Chaotropic salts include guanidine hydrochloride, guanidine thiocyanate (which is sometimes referred to as guanidine isothiocyanate), sodium iodide, sodium perchlorate, and sodium trichloroacetate. Preferred are the guanidinium salts, more preferably guanidine hydrochloride or guanidine thiocyanate, but most preferably guanidine thiocyanate (GTC).

With any chaotropic salt used in the invention, it is desirable that the concentration of the salt, in any of the solutions in which the salt is employed in carrying out the invention, remain below the solubility of the salt in the solution under all of the conditions to which the solution is subjected in carrying out the invention.

The preferred embodiments of the methods of the present invention use a silica matrix to isolate RNA from a cleared lysate produced according to the pre-treatment methods of this invention. The silica matrix used in the preferred methods is preferably a silica matrix incorporated into a filter basket, to isolate RNA. The silica matrix is more preferably incorporated into at least one filter disk fitted into the base of the filter basket used in the present methods, and the resulting filter basket assembly is even more preferably configured to give the user the option of processing solutions placed in the filter basket using centrifugal force, or vacuum filtration, or a combination of the two. The most preferred filter disk used in the filter basket is a filter disk impregnated with silica, such as SPEC™ silica disks commercially available from Ansys Corporation, Irvine, Calif., USA. Only the most preferred filter basket assembly and silica matrix and their use in the methods of the present invention are specifically described below. However, the present invention is not limited to either the particular form of silica matrix or the particular basket assembly configuration discussed below.

The methods of the present invention can be used to isolate RNA from any one of a number of different sources of biological material. Such sources include eukaryotic or prokaryotic cells in culture form or in the form of cells taken or obtained from various tissues. Biological material which may be processed according to the present methods also include: plant or animal tissue; bodily fluids from animals including blood, lymph, urine, feces, or semen; or tissue from embryos or fetuses. The biological material from which RNA is isolated according to the methods of the present invention is preferably in the form of cells or tissue, such as the types of materials described above, but it can also be in the form of organelles, viruses, phages, plasmids, viroids or the like that infect cells. Regardless of what type of biological material is used, the present method of isolating RNA from such material begins with the disruption of the material in the presence of a lysis solution, thereby causing any RNA present in the material to be released into the solution. The biological material can be disrupted in this first step of the present method using any one of a number of different techniques familiar to those in the art to obtain lysate solutions from which RNA can be isolated. The RNA in any such lysate solution will typically be found with other components, including proteins, lipids, and DNA.

In order to isolate RNA from any solution using a silica matrix according to the preferred embodiments of the methods of the present invention, the RNA must be present in a form in which it is available to bind to the silica matrix used in the method, such as the silica impregnated into the filter disk component of the preferred filter basket assembly. In cases where RNA is isolated from solutions with relatively few contaminants, such as run-off transcription products or solutions of partially isolated RNA obtained from other sources, one need only add alcohol and adjust the concentration of chaotropic salt in the solution to a level necessary to ensure binding of RNA to the matrix prior to addition to the filter basket and further processing in accordance with the remaining steps of the method described below. However, when RNA is isolated from samples of more complex sources of RNA, such as tissue culture cells, plant or animal tissue, yeast, bacteria, and fungi, the samples must be processed before being placed into contact with the silica matrix to remove at least some of the proteins and lipids likely to interfere with adhesion of the RNA to the matrix. The additional steps necessary for practicing the present methods of isolating RNA from such complex sources are described further below.

The first step in processing any complex biological material, such as blood cells or animal tissue, is to disrupt the material in order to release any RNA contained therein. The particular technique chosen to release RNA from a cell will depend upon the nature of the cell containing the material. For example, mechanical disruption is topically required in order to ensure the release of RNA from cells or tissue with relatively hard cell walls, such as fungus cells or plant tissue. In order to sufficiently disrupt such cells to cause the release of RNA contained therein, one must at least homogenize the cells in the presence of a lysis buffer. Sometimes, additional treatment prior to or subsequent to homogenization is also required in order to release RNA into the lysis buffer, such as predigestion of the cell walls with a protease, or exposure to the disruptive force of a sonicator. Contrastingly, RNA can be readily released from cells with lipid bi-layer membranes such as *E. coli* bacteria or eukaryotic tissue culture cells merely by adding a lysis buffer to the cells.

The lysis buffer used to disrupt any biological material precessed to isolate RNA according to the methods of the present invention must contain a chaotropic salt, such as guanidine thiocyanate, preferably at a salt concentration of least 2 M and more preferably at a concentration of at least 4 M. The lysis buffer used in the present methods can also contain a detergent, in which case the detergent is preferably a mild non-ionic such as sodium laryl sarcosine (SDS). The lysis buffer is preferably buffered to a pH between 6 and 8.5, more preferably buffered to a pH of about 7.5. RNase inhibitors in addition to the chaotropic salt can also be added to the lysis buffer or to other solutions used in later steps of the method of the present invention, including but not limited to β-mercaptoethanol.

Once the target RNA is released from biological material lysed or disrupted as described above, the resulting lysate solution has a high concentration of cellular debris and other contaminants, including DNA and proteins, likely to interfere with the adhesion of the target RNA to the silica matrix in subsequent processing steps of the present method. The lysate solution is then diluted by the addition of a dilution buffer to the solution. Surprisingly, when one adds a dilution buffer to a lysate solution such as the solution described above, a significant amount of the contaminants, including protein and DNA, drop out of solution in the form of a precipitate. Even more surprisingly, higher yields of RNA are obtained on isolation of RNA from a lysate solution using a silica matrix to bind and release the RNA therefrom when the lysate solution is first cleared according to the pre-treatment steps of the present method than when no pre-clearance steps are used. Thus, the present method of RNA isolation enable one to isolate higher yields of RNA of higher purity than those isolated using existing systems and methods, e.g. the RNeasy Spin Column from QIAGEN® (see Examples 4–6, below).

The dilution buffer used to dilute the lysate solution in this step of the method can be plain water, but it preferably also contains salt and a buffer, such as one of the commonly employed mixtures of sodium chloride and sodium citrate with a pH of about 7.0 (i.e. an "SSC" solution), preferably an SSC buffer with a concentration of at least 6×, more preferably an SSC buffer with a concentration of at least about 20×. See *Molecular Cloning* ed. by Sambrook et al., 2nd ed., vol. 3 (1989) page B.1 3 for the composition of a 20× SSC solution. The dilution buffer more preferably contains a salt, a buffer, and a detergent, such as sodium lauryl sulphate (SDS). When the dilution buffer includes a salt, the salt is preferably sodium chloride.

In the next of the initial processing steps of the method, the precipitate and particulate cellular debris are removed from the diluted lysate solution using any one of a number of different removal methods, such as filtration or centrifugation, but more preferably by centrifugation. The size of the pellet obtained by centrifuging the diluted lysate solution is at least twice as large as the pellet one would obtain from centrifuging the same lysate solution without dilution. The size of the pellet obtained after dilution and centrifugation depends upon the complexity of the biological material lysed in the first step of the method. When centrifugation is used to remove the precipitated contaminants and cell debris in a first container, the supernatant is then transferred from the first container in to a second container, preferably transferring the supernatant by decantation or by pipetting, leaving the pellet of contaminants and debris in the first container. The resulting cleared lysate solution is then ready for further processing, according to any one of a number of different methods, but preferably according to the following steps.

As noted above, the solution from which the target RNA is isolated according to preferred methods of the present invention need not be a solution of target RNA released directly from cells. The target RNA in the solution can be the product of transcription of target RNA from a DNA template, such as run-off transcription of a plasmid vector with an RNA polymerase promoter using RNA polymerase and an appropriate promoter primer. The target RNA can also be in the form of a mixture of melted or enzymatically digested electrophoresis gel and nucleic acid material. The solution processed according to the present methods can also be a solution of one particular species of RNA, such as mRNA, in partially isolated form.

Whether in the form of a cleared lysate, prepared as described above, or in the form of less contaminated solution of RNA such as the solutions described immediately above, the solution to be processed according to the present method is treated in the next step as follows. A reagent mixture containing at least one binding enhancer, preferably a binding enhancer selected from the group consisting of a chaotropic salt, a non-chaotropic salt such as sodium chloride, and an alcohol is added to the solution from which RNA is to be isolated. The reagent mixture preferably contains a sufficient amount of at least one binding enhancer to raise the concentration of binding enhancer in the RNA solution to a level sufficiently high to ensure the binding of any nucleic acids in the solution to the silica matrix used to isolate the RNA from the solution in subsequent steps of the method.

The reagent mixture used in the second step of the method is preferably a mixture of alcohol and a chaotropic salt. The concentration of chaotropic salt in this preferred form of the reagent mixture is preferably between about 1 M and 6 M, more preferably between about 2 M and 5 M, and most preferably between about 2 M and 3 M. The chaotropic salt is preferably guanidine thiocyanate. The concentration of chaotropic ions in the mixture is preferably sufficiently high to inactivate RNases and to promote the disruption of nucleo-protein complexes in the mixture, particularly RNA-protein complexes. The amount of alcohol in this preferred form of the reagent mixture is preferably sufficient to cause RNA to selectively precipitate out of the solution. The alcohol in the mixture is preferably a low molecular weight alcohol, such as ethanol or isopropanol, but is more preferably ethanol.

Once the reagent mixture has been added to the cleared lysate or other RNA containing solution, the resulting binding mixture is placed in contact with the silica matrix. When the silica matrix is in the form of a silica disk in the base of a filter basket, then the reagent mixture is placed into contact with the silica matrix in the silica disk by being placed into the filter basket. The most preferred form of the silica matrix used in the present method is used herein below to illustrate the remaining steps of the method. However, the present invention is not limited to this preferred silica matrix configuration.

Once the RNA in the mixture has formed a complex with the silica matrix, preferably by adhering to the silica disk(s) in the filter basket, the remaining material in the mixture can then be removed from the silica matrix, preferably using either a vacuum or centrifugal force, or using a combination of the two types of force.

Figure 1:
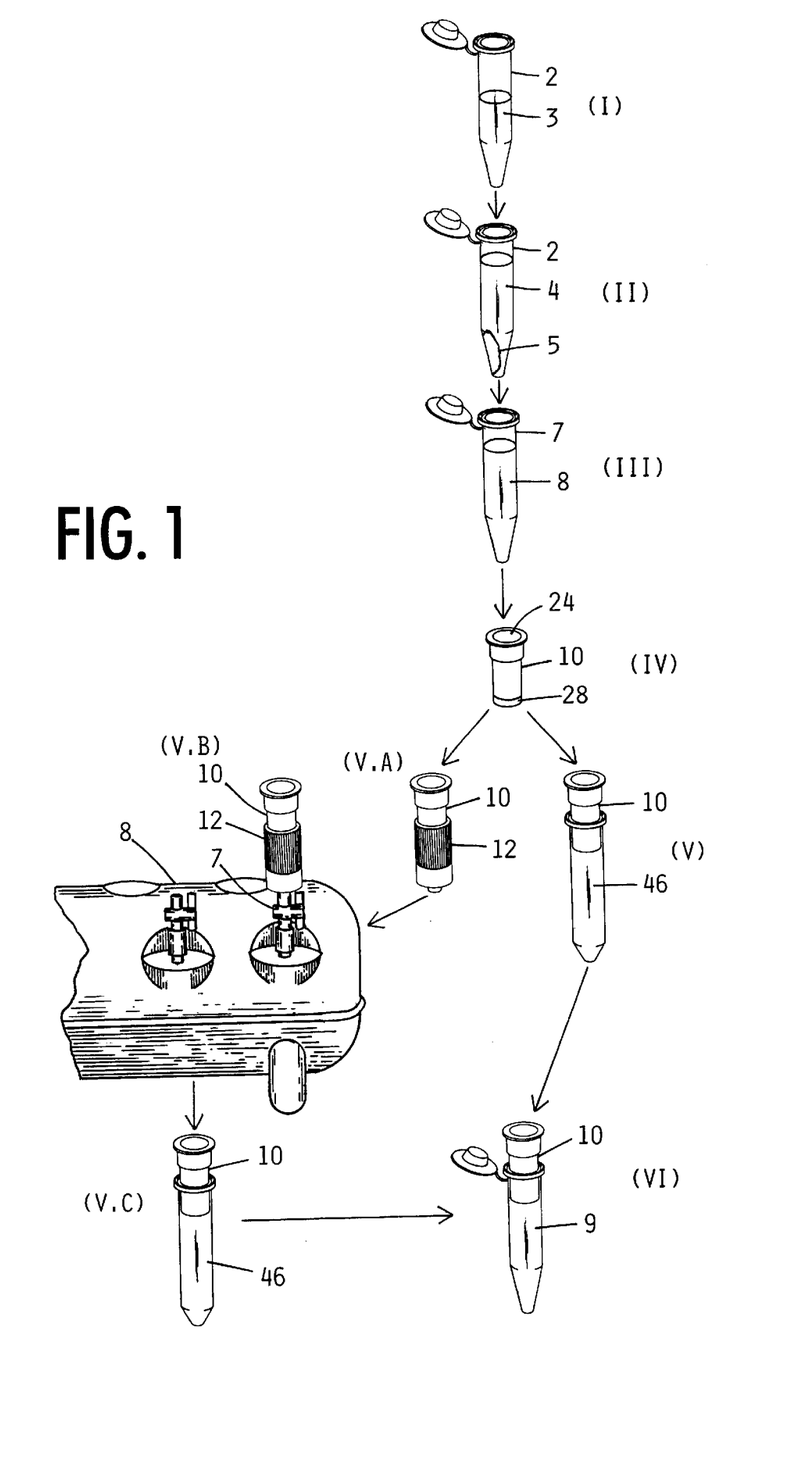
FIG. 1 is a flow diagram of a preferred aspect of the method of isolating RNA of the present invention, wherein: biological material is lysed; diluted to precipitate contaminants, centrifugation is used to remove the precipitate formed therein; and RNA is isolated from the resulting cleared lysate using a filter basket designed for removal of solutions contained therein by vacuum filtration (left path in the diagram) or by spin filtration (right path in the diagram).

FIG. 1 is a flow diagram illustrating the use of the most preferred filter basket assembly configuration used to isolate RNA from a biological material according to a particularly preferred embodiment of the methods of the present invention, wherein vacuum filtration (the left pathway of the diagram), or centrifugation (the right pathway of the diagram) is used to remove solutions from a filter basket and silica matrix contained therein at various points in the method. Step I of the diagram shows a lysate of biological material 3 in a first container 2. Step II shows the lysate solution after dilution to precipitate contaminants, and after centrifugation to remove the precipitate and cell debris from the solution. The first container 2 in Step II is shown with a cleared lysate solution 4 and a pellet 5 of precipitate and other contaminants. Step III shows the cleared lysate after it has been transferred to a second container 7, and after a reagent mixture with at least one binding enhancer has been added to the cleared lysate to form a binding mixture 8. In Step IV, the binding mixture is transferred to filter basket 10 through the open end 24 at the first end of the filter basket. The RNA and some other nucleic acid materials contained in the solution then bind to a silica matrix, in the form of a filter disk(s) 28, at the base end of the filter basket. The mixture is then removed from the filter basket, using either of the two paths depicted in Step V of FIG. 1, one in which centrifugation is used to remove the solution, and the other in which vacuum filtration is used for removal.

The centrifugation pathway is depicted as a single Step V on the right hand branch of the diagram of FIG. 1. In that step, the second end of the filter basket 10 is inserted into a collection tube 46, and then spun in a centrifuge so that essentially all of the mixture in the filter basket 10 flows down into the collection tube 46. The filter basket 10 is then removed from the collection tube 46, the mixture collected therein is discarded, and the filter basket 10 is placed once again in the collection tube 46. A wash mixture is then added to the filter basket, and the resulting filter basket and collection tube assembly is spun again to remove the mixture from the filter basket. The wash step can be repeated as many times as desired. When the wash steps are completed, and the assembly has been spun for the last time, the filter basket is transferred to a sterile final collection tube 9, as depicted in Step VI. An elution solution is then added to the filter basket 10, a solution designed to release the target RNA bound to the silica filter disk(s) contained therein. The elution solution containing the released target RNA is then transferred from the filter basket 10 into the final collection tube 9 using centrifugal force.

The vacuum filtration pathway is shown on the left side of FIG. 12, in the form of three substeps of Step V. In the first substep, Step V.A, the second end of filter basket 10 is inserted into the opening 36 in the first end 30 of vacuum manifold adapter 12, forming a substantially airtight seal therewith. In the second substep, Step V.B., the vacuum manifold adapter 12 is mounted onto a Luer-Lok® port 7 of a Vac-Man® laboratory vacuum manifold 8, and vacuum pressure is used to draw the mixture out of the filter basket 10 and into the vacuum manifold 8. The filter basket 10 is washed at least once by adding a wash solution to the basket and using vacuum pressure to draw the wash solution out to the filter basket 10 and into the vacuum manifold 8. Finally, in the third substep, Step V.C, the filter basket 10 is removed from the vacuum manifold adapter 12 and placed in a collection tube 46, where it is spun to remove any solution remaining in or on the surface of the filter basket. The filter basket 10 is then transferred to a final sterile collection tube 9, and the target RNA bound to the silica filter disk(s) is eluted therefrom using the same type of elution step (Step VI) described for the centrifugation pathway described immediately above.

The wash solutions used in the washing steps of the methods of RNA isolation of the present invention are all done using wash solutions designed to remove material from the filter basket and from the silica filter disks contained therein without removing the target RNA bound thereto, regardless of whether centrifugal or vacuum force is used to remove the wash solution from the filter basket. The wash solutions used in the present method preferably comprise a salt and a solvent, preferably an alcohol. The concentration of alcohol in this last preferred form of the wash solution is preferably at least 30% by volume, more preferably at least 40% by volume, and most preferably at least 50% by volume. The alcohol so used is preferably ethanol or isopropanol, more preferably ethanol. The salt is preferably in the form of a buffer, and most preferably in the form of an acetate buffer.

In a particularly preferred embodiment of the method of the present invention, an RNase-free solution of deoxyribonuclease (DNase) is used to digest any DNA contaminants in the sample to be isolated. In cases where no lysis step is required, for example when the sample from which RNA is to be isolated is not contained within a cell or similar biological material, then the sample can be digested with DNase prior to adding chaotropic salt and loading the sample on the Spin Basket for further processing. However, when the RNA is isolated from a lysate, the DNase treatment step is preferably done either in the Spin Basket itself after at least one wash step or in the final isolated sample after the RNA is eluted from the Spin Basket.

The DNase treatment step is most preferably done in the Spin Basket after at least one wash step, as described below. The DNase treatment step is initiated by adding an RNase-free solution of DNase enzyme suspended in a DNase incubation buffer, in which the enzyme is active, but more preferably by adding a DNase enzyme suspended in a DNase incubation buffer solution in which the enzyme is optimally active, such as a low salt buffer. When less than optimal buffer conditions are used, one must add larger quantities of DNase to digest the same amount of DNA contaminants in the filter basket. The DNase incubation buffer is preferably buffered to be a pH of at least 7 and up to 9. The DNase incubation buffer also preferably contains at least about 1 mM magnesium chloride and up to about 1M of sodium chloride more preferably a sodium chloride of about 100 mM.

The filter basket and DNase solution are then allowed to incubate for a sufficient amount of time after DNase addition for the DNase to react with and digest any DNA remaining in the filter basket, including any DNA bound to the silica filter disk(s). The incubation period preferably lasts at least one minute, more preferably for at least 5 minutes, and most preferably for at least 15 minutes.

When the incubation period is over, a chaotropic salt mixture is preferably added to the basket to adjust the solution conditions to conditions which favor formation and retention of the RNA/silica matrix complex. The chaotropic salt component of the mixture also inherently inactivates the DNase, and any other enzymes remaining in the basket. The chaotropic salt mixture preferably further comprises alcohol, preferably ethanol. The resulting inactivated incubation mixture is then removed from the filter basket using vacuum filtration or centrifugation as described above, and the basket is washed at least once after the DNase treatment step using a wash solution as described above.

The elution solution used to elute the RNA from the silica matrix complex in the elution step of the present method is preferably an aqueous solution of low ionic strength, more preferably water or a low ionic strength buffer at about a pH at which the nucleic acid material is stable and substantially intact. Any aqueous solution with an ionic strength at or lower than TE buffer (i.e. 10 mM Tris-HCl, 1 mM ethylenediamine-tetraacetic acid (EDTA), pH 8.0) is suitable for use in the elution steps of the present methods, but the elution solution is preferable buffered to a pH between about 6.5 and 8.5, and more preferably buffered to a pH between about 7.0 and 8.0. TE Buffer and distilled or deionized water are particularly preferred elution solutions for use in the present invention. The low ionic strength of the preferred forms of the elution solution described above ensures the nucleic acid material is released from the particle. Other elution solutions suitable for use in the methods of this invention will be readily apparent to one skilled in this art.

The RNA eluted from the filter basket using the method of the present invention is suitable, without further isolation, for analysis or further processing by molecular biological procedures. The eluted RNA can be sequenced or analyzed directly using gel electrophoresis. The eluted RNA can also be analyzed using nucleic acid probe hybridization, or reverse transcribed using a reverse transcriptase polymerase chain reaction (RT-PCR). Thus, the methods of the invention can be applied as part of methods, based on analysis of RNA, for, among other things, diagnosing diseases; identifying pathogens; testing foods, cosmetics, blood or blood products, or other products for contamination by pathogens; forensic testing; paternity testing; and sex identification of fetuses or embryos.

The following, non-limiting examples teach various embodiments of the invention. Except where indicated otherwise, the filter basket assembly used in the examples below was a Wizard® Plus SV Minipreps Spin Column, referred to below simply as the "Spin Column". The vacuum adapter component of that assembly used below is referred to below as a Miniprep Vacuum Adapter. It is to be understood that these examples are merely a few of the various embodiments or aspects of the methods of the present invention. It is likely that many more embodiments of the present invention will occur to one skilled in this art in light of the teachings herein.

EXAMPLE 1

Reagent Preparation

The following solutions were prepared or obtained for use in the procedures performed in the remaining Examples, below:

Lysis Buffer

4M Guanidine thiocyanate 0.01 M Tris pH 7.5

0.974% β-mercaptoethanol (20 µl/ml Lysis Buffer)

The β-mercaptoethanol was not added to the Lysis Buffer until shortly before the Lysis Buffer was used to lyse or homogenize the tissue samples as described below.

Dilution Buffer

20× SSC 0.25% N-lauroyl sulphate (SDS)

A sterile 20× SSC stock solution was prepared as described in *Molecular Cloning*, Vol. 3, by Sambrook, et al., p. B.1 3 (Cold Spring Harbor Press, 1989). The 20× stock solution was then diluted with SDS and sterile RNase-free water to the final concentrations of SSC and SDS, above.

DNase Solution 3,500 units DNase I (lyophilized) suspended in 5 µl of water; and 45 µl DNase Buffer (0.04M Tris, pH 8; 0.01 M NaCl; 0.006M $MgCl_2$; and 0.01 M $CaCl_2$).

This solution was aliquotted into convenient sized portions. Unused portions were stored at −20° C.

Column Wash Solution

A concentrated aqueous Tris-Acetate stock solution is prepared having 162.8 mM potassium acetate, and 27.1 mM Tris-HCl, pH 7.5. Ethanol (EtOH) is then mixed with the Tris-Acetate stock solution for a final wash solution concentration of:

60% EtOH 60 mM $KOA_c$, and 10 mM Tris-HCl pH 7.5.

EXAMPLE 2

Tissue samples were prepared from various organs, pooled together, from several mice for processing according to the same RNA isolation procedure described below, so the amounts and purity of RNA isolated from each organ according to that method could be compared to one another.

One set of cleared lysate solutions were prepared for application to a Spin Column from six 30 milligram samples each of mouse Liver, Kidney, Brain, Lung, and Spleen tissue, by following the following steps:

1. Each type of tissue was homogenized by adding 175 µl of Lysis Buffer per 30 mg wet weight of tissue.
2. The homogenized tissue was then aliquoted out into at least six aliquots of 175 µl each per type of tissue homogenized in aliquoted into a 1.5 ml microcentrifuge tube. 350 µl of Dilution Buffer pre warmed to 70° C. was then added to each aliquot. Each tube was then capped, and the contents of each tube mixed by inverting each tube two or three times.
3. The microcentrifuge tubes were transferred to a microcentrifuge and centrifuged for 5 minutes at high speed. The supernatant was then transferred to a fresh microcentrifuge tube by decanting. The final volume of solution transferred was about 500 µl per tube.
4. 235 µl of 95% EtOH Reagent was then added to each sample, and mixed by inversion.
5. The entire contents of each sample tube were then transferred to a spin basket by decanting, and the RNA in each sample was isolated by either vacuum filtration or by centrifugation according to the process described in either of the next two Examples.

The samples prepared as described above were then transferred to Spin Baskets and processed by spin filtration to isolate RNA therefrom, by following the procedure described below and the reagents prepared as described in Example 1, above:

1. Each Spin Basket was inserted into a collection tube. The Basket/Tube assembly was then inserted into a microcentrifuge and spin at high speed for one minute. By the end of the spin cycle, all the solution in the spin basket appeared to have transferred to the collection tube. The contents of the collection tube were discarded, and each Spin Basket was reinserted into its corresponding collection tube for further processing.
2. 600 µl of wash solution was added to each Spin Basket, and the assembly was centrifuged again at high speed for one minute. The contents of each collection tube were once again discarded, and the Spin Basket reinserted into the tube.
3. The collection tube/basket assemblies were then placed in a tube rack.

For each prep to be performed, a mixture of 45 µl DNase Buffer and 5 µl DNase enzyme was prepared. 50 µl of this freshly prepared DNase solution was then added to each Spin Basket, and the assemblies were incubated at room temperature for 15 minutes.

4. At the end of the incubation period, 600 µl of 2.19 M GTC Solution was added to each Spin Basket. Each Spin Basket/collection tube assembly was then centrifuged at high speed for one minute. The contents of the collection tube were discarded and the Spin Basket reinserted therein.
5. 600 µl Column Wash Solution was then added to each Spin Basket, and the assembly was centrifuged again at high speed for one minute. The contents of the collection tube were discarded and the Spin Basket reinserted therein
6. 250 µl of Column Wash Solution was added to each Spin Basket, and the assembly centrifuged at high speed for two minutes.

7. The Spin Basket was then transferred to a fresh sterile tube. 100 μl of Nuclease-Free Water was added to each Spin Basket to elute the RNA from the Spin Basket filter, and the Basket and fresh sterile tube were centrifuged at high speed for one minute.
8. The resulting eluent solution of isolated RNA was stored at 4° C. or colder.

EXAMPLE 3

Six isolated RNA samples prepared from each of five different mouse tissues as described in Example 2 were then analyzed spectrophotometrically to determine the yield and purity of each RNA sample obtained thereby. Specifically, yield was determined by measuring the absorption of an aliquot of RNA at 260 nm, where one absorbance unit ($A_{260}$) indicates concentration of 40 μg of single-stranded RNA per milliliter of solution. Relative absorbance at 230, 260, and 280 nm are also known to be good indicators of purity.

Table 1, below shows the purity and yield results obtained from testing the various tissue samples processed using the centrifugation procedure described in Example 2, above. Each of the figures in Table 1 is an average of the results obtained from all six samples of RNA obtained from each tissue. A standard deviation figure is provided in parenthesis after each yield figure in the table.

TABLE 1

Isolation of RNA from Various Tissues

| Tissue | Yield μg/mg tissue | Std. Dev. | 260/280 | 260/230 |
|---|---|---|---|---|
| Mouse Liver | 3.19 | (0.13) | 2.07 | 2.17 |
| Mouse Kidney | 1.88 | (0.18) | 2.08 | 2.18 |
| Mouse Brain | 0.24 | (0.10) | 2.68 | 1.50 |
| Mouse Lung | 0.45 | (0.23) | 2.08 | 1.63 |
| Mouse Spleen | 1.09 | (0.26) | 2.09 | 2.07 |

The 260/280 and 260/230 ratio results in Table 1, above all indicate the RNA isolated from the various tissues according to the procedures of Examples 1 and 2 is free of contaminants, particularly free of the type of contaminants likely to lower those ratio figures below 2.0. The 260/280 ratio is used to detect protein contaminants, while the 260/230 ration is typically used to detect trace amounts of guanidine thiocyanate. If present in a sample of isolated RNA, either or both forms of contaminants could interfere with downstream processing or analysis. The yield results obtained from each tissue sample processed in Example 3 are comparable to or higher than results of obtained from the same types of tissues using other RNA isolation techniques.

EXAMPLE 4

Three sets of six 30 mg. samples of mouse liver tissue were processed to isolate total RNA therefrom using three different procedures and two different sets of reagents. In the first such procedure, RNA was isolated using the Wizard® Plus SV Minipreps Spin Column and centrifugation according to the same method used in Example 2, above. The second procedure used the same type of Spin Column and same reagents to isolate RNA from the mouse liver samples using vacuum filtration. Finally, in the third procedure, reagents were prepared as described in the RNeasy™ Handbook and used according to the procedures described in that handbook with an RNeasy Spin Column to isolate RNA, as recommended by the vendor of that RNA isolation system, i.e. QIAGEN®.

The first set of six samples of liver tissue were processed according to the same procedure described in Example 2, above.

The second set of six samples of liver tissue were processed for application to Spin Columns according to the same procedure used in Example 2. However, instead of processing the samples applied to the Spin Columns using centrifugation, vacuum filtration was used, as follows:

1. The Spin Basket was placed on a manifold adaptor and mounted on a vacuum manifold. Vacuum pressure was then used to draw all the solution out of the Spin Basket and into the manifold.
2. 900 μl of Column Wash Solution was added to each Spin Basket and similarly drawn through the Spin Basket filter into the manifold using vacuum pressure. This wash step was repeated once.
3. The vacuum was then turned off, and an unused port used to vent the vacuum pressure from the manifold. When all the vacuum pressure appeared to have been released from the manifold, a DNase solution was added to each Spin Basket. For Spin Basket to be treated, a DNase solution of 45 μl DNase Buffer and 5 μl DNase enzyme was prepared immediately before use. 50 μl of this freshly prepared DNase solution was added to each Spin Basket, and incubated at room temperature for 15 minutes.
4. At the end of the incubation period, 600 μl of 2.19 M GTC Solution was added to each basket. The unused vacuum manifold port was then closed, and vacuum was applied again for the solution to run through into the manifold.
5. 900 μl of Column Wash Solution was applied to each Spin Column and run through. The same wash procedure was repeated a second time.
6. The Spin Basket was then removed from the vacuum manifold adapter and inserted into a collection tube. The resulting basket/tube assembly was then placed in a microcentrifuge and spun at high speed for two minutes.
7. The Spin Basket was then transferred to afresh sterile tube. 100 μl of Nuclease-Free Water was added to each Spin Basket to elute the RNA from the Spin Basket filter, and the Basket and fresh sterile tube were centrifuged at high speed for one minute.
8. The resulting eluent solution was stored at 4° C. or colder.

The third set of six samples of mouse liver tissue were processed using the method, reagents, and spin column from the RNeasy Total RNA Purification Protocols using the RNeasy Spin Columns.

EXAMPLE 5

The amount and quality of RNA isolated from the variety of different sources and using the isolation procedures described in Example 4 were assayed spectrophotometrically, using the same assay technique as described in Example 3, above. The spectrophotometric results obtained from the RNA isolated with each procedure described in Example 4, above are presented in Tables 2–4, below, and summarized in Table 5, below.

TABLE 2

Promega Spin

| No | Absorption at: | | | 260/ 280 | 260/ 230 | Conc in µg/ml | Yield in µg/100 µl |
|---|---|---|---|---|---|---|---|
| | 230 nm | 260 nm | 280 nm | | | | |
| S1 | 0.880889 | 1.95104 | 0.940521 | 2.07 | 2.21 | 975.2 | 97.6 |
| S2 | 0.855758 | 1.86453 | 0.899795 | 2.07 | 2.18 | 932.3 | 93.2 |
| S3 | 0.93753 | 2.0509 | 0.998153 | 2.05 | 2.19 | 1025.5 | 102.5 |
| S4 | 0.847351 | 1.87686 | 0.901473 | 2.08 | 2.21 | 938.4 | 93.8 |
| S5 | 0.834716 | 1.86016 | 0.894607 | 2.08 | 2.23 | 930.1 | 93.0 |
| S6 | 0.826644 | 1.84858 | 0.886123 | 2.09 | 2.24 | 924.3 | 92.4 |

TABLE 3

Promega Vacuum

| No | Absorption at: | | | 260/ 280 | 260/ 230 | Conc in µg/ml | Yield in µg/100 µl |
|---|---|---|---|---|---|---|---|
| | 230 nm | 260 nm | 280 nm | | | | |
| V1 | 1.38282 | 2.53215 | 1.27543 | 1.99 | 1.83 | 1266.1 | 126.6 |
| V2 | 1.28326 | 2.51055 | 1.27079 | 1.98 | 1.96 | 1255.3 | 125.5 |
| V3 | 1.36996 | 2.52447 | 1.2604 | 2.00 | 1.84 | 1262.2 | 126.2 |
| V4 | 1.21948 | 2.46383 | 1.24165 | 1.98 | 2.02 | 1231.9 | 123.2 |
| V5 | 1.24266 | 2.53387 | 1.25479 | 2.02 | 2.04 | 1266.9 | 126.7 |
| V6 | 1.34949 | 2.60375 | 1.28459 | 2.03 | 1.93 | 1301.9 | 130.2 |

TABLE 4

Qiagen (Spin)

| No | Absorption at: | | | 260/ 280 | 260/ 230 | Conc in µg/ml | Yield in µg/100 µl |
|---|---|---|---|---|---|---|---|
| | 230 nm | 260 nm | 280 nm | | | | |
| Q1 | 0.628936 | 1.32658 | 0.68962 | 1.92 | 2.11 | 663.3 | 66.3 |
| Q2 | 0.668762 | 1.458 | 0.775894 | 1.88 | 2.18 | 729.0 | 72.9 |
| Q3 | 0.750732 | 1.67729 | 0.883789 | 1.90 | 2.23 | 838.6 | 83.9 |
| Q4 | 0.789428 | 1.71302 | 0.898437 | 1.91 | 2.17 | 856.5 | 85.7 |
| Q5 | 0.628036 | 1.4522 | 0.781402 | 1.86 | 2.31 | 726.1 | 72.6 |
| Q6 | 0.725631 | 1.67994 | 0.884155 | 1.90 | 2.32 | 840.0 | 84.0 |

TABLE 5

Summary of Results

| Method used to Isolate RNA | Yield µg/mg tissue | Std. Dev. | 260/ 280 | 260/ 230 |
|---|---|---|---|---|
| Spin Basket - Spin | 3.18 | (0.13) | 2.07 | 2.21 |
| Spin Basket - Vacuum | 4.21 | (0.07) | 2.00 | 1.94 |
| QIAGEN - Spin | 2.59 | (0.27) | 1.90 | 2.22 |

The results in Tables 2–5, above, clearly indicate both the centrifugation and vacuum filtration methods of RNA isolation using the Spin Basket produced significantly higher yields and RNA which is at least as free of contaminants as RNA produced using the QIAGEN spin column and method.

Figure 3:
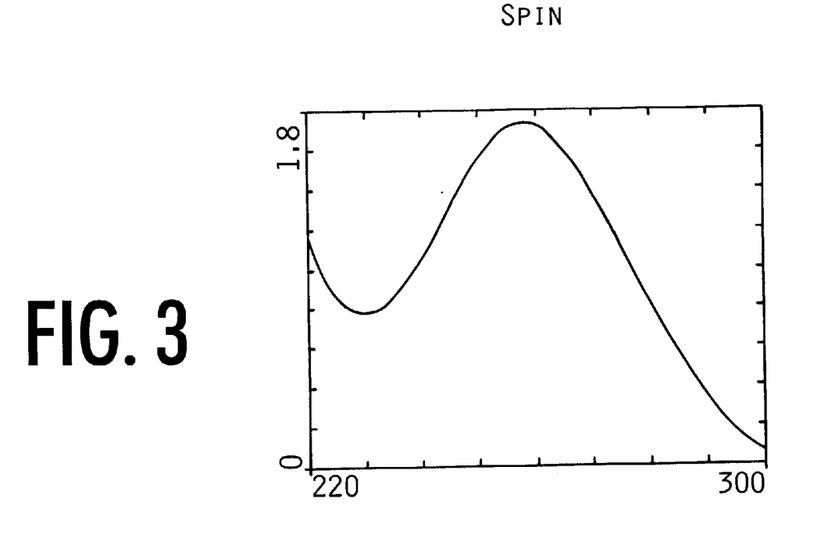
FIG. 3 is a spectrum of the absorbence, from 220 to 300 nm, of a sample of RNA isolated from mouse liver tissue using a Wizard® Plus SV Spin Filter and centrifugation.
Figure 4:
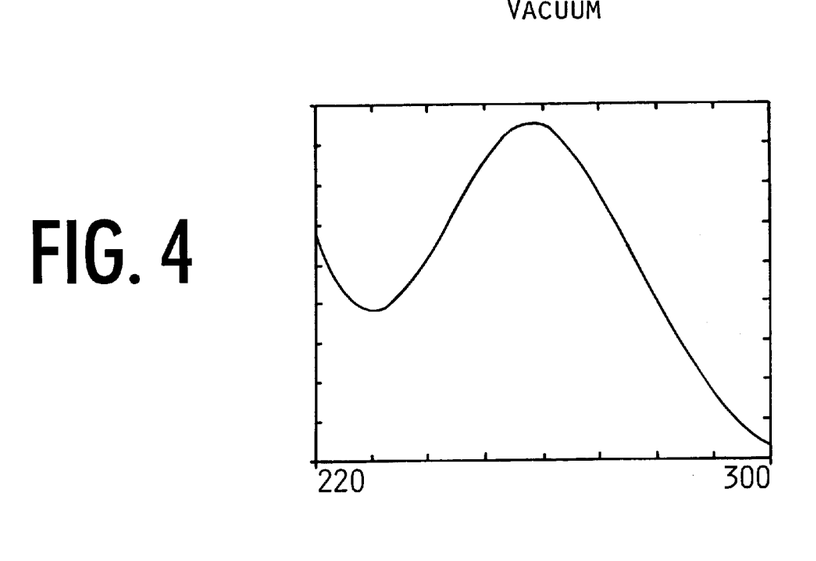
FIG. 4 is a spectrum of the absorbence, from 220 to 300 nm, of a sample of RNA isolated from mouse liver tissue using a Wizard® Plus SV Spin Filter and vacuum filtration.

One sample each of RNA isolated from 30 mg. of mouse liver using centrifugation and one sample isolated using vacuum filtration using the Wizard® Plus SV Minipreps Spin Column according to the method of Example 4, above, was scanned with a spectrophotometer. The results obtained by scanning the sample of RNA isolated using centrifugation is shown in FIG. 3, while the results obtained by scanning the sample of RNA isolated using vacuum filtration is shown in FIG. 4. Like the other spectrophotometric results shown in Tables 2–4 and summarized in Table 5, above, the scans in FIGS. 3 and 4 show a smooth curve with a peak at about 260 nm, the expected maximum absorbance for a nucleic acid, and no detectable distortions in the shape of the curve at wavelengths where one would expect to see proteins (i.e. at about 280 nm) or at wavelengths where one would expect to see guanidine ions (i.e. at about 230 nm). In other words, the spectrophotometric scan results are consistent with the individual peak and ratio results summarized in Table 5, above.

EXAMPLE 6

One microgram of each of the 18 samples of total RNA isolated from mouse liver tissue as described in Example 4, above, were used as templates in reverse transcriptase polymerase chain reactions (RT-PCR) and the resulting reaction products were analyzed using gel electrophoresis, as described below. The primer pair selected for this assay is a primer pair which hybridizes to an encoding region of the Interleukin I gene of mouse genomic DNA which flanks at least one intron. The primers used in this particular assay were the Mouse 5' IL-1β Primer (5'-AAG GAG AAC CAA GCA ACG AC-3') and the Mouse 3' IL-1β Primer (5'-GAG ATT GAG CTG TCT GCT CA-3').

Each of the 1 μg samples of isolated RNA was processed as follows:
1. First strand cDNA transcripts were prepared from each of the RNA samples by incubating each sample at 37° C. in a sealed microtiter plate for 30 minutes in the presence of a cDNA reagent mix, consisting of:
   7.4 μl of 10× RT 9600 Gold Buffer (Promega) (40 mM Tris-HCl, pH 7.95 at 22° C., 0.2 M KCl, 6 mM MgCl$_2$, 8 mM DTT, and 0.21 % by volume of yellow dye).
   0.15 μl of 10 mM each of all four dNTP's
   1.2 μl of Oligo(dT)$_{15}$ Primer (0.6 mg)
   0.75 μl of RNasin® Ribonuclease Inhibitor (30 u) (Promega)
   0.5 μl of AMV Reverse Transcriptase (10–1 2.5 u)
2. The cDNA synthesis reaction was stopped by heat inactivation at 95° C. for 5 minutes, followed by chilling on ice for 5 minutes.
3. Condensate which formed on the inside cover of the microtiter plate during the above steps was collected in the wells of the plate by centrifugation.
4. 5 μl of each solution of first strand cDNA prepared above was transferred to a microtube, and 45 μl of a PCR Mix was added to each microtube. Each 45 μl of PCR Mix contained the following components:
   33.8 μl of Sterile, Nuclease-Free Water
   5 μl of 10× PCR Buffer (0.1 M Tris-HCl, pH 8.3 at 20° C., 15 mM MgCl$_2$, and 0.5 M KCl.)
   0.975 μl of 10 mM each of all four dNTP's
   2.5 μl of 20 μM Mouse 3' IL-1β Primer
   2.5μl of 20 μM Mouse 5' IL-1β Primer
   0.25 μl of Taq DNA Polymerase (1.25 u)
5. The microtubes of first strand cDNA and PCR Mix were then sealed, transferred to a thermocyler, and cycled through the following temperature conditions to amplify the RNA and cDNA contained therein:
   Pre-warming: Single 1 minute incubation at 95° C.,
   Thermocycling: 94° C. for 30 sec., 60° C. for 15 sec., and 70° C. for 30 sec., for a total of 35 cycles, and
   Post-cycling Treatment: 72° C. for 5 minutes.
6. At the end of the final post-cycling treatment step, the microtubes were transferred to wet ice, and allowed to cool at 4° C. until the results of the reaction could be evaluated at the next step.
7. The products of the RT-PCR reaction, above were then analyzed by gel electrophoresis, as follows. 10 μl of a 6× Loading Dye solution was added to each 50 μl PCR sample, above. The resulting mixture was then loaded on a 1.5% agarose gel. The gel was electophoresed at 200 Volts for 1 hour, and then stained with a fluorescent dye and analyzed using an automated Fluorimager.

Figure 2:
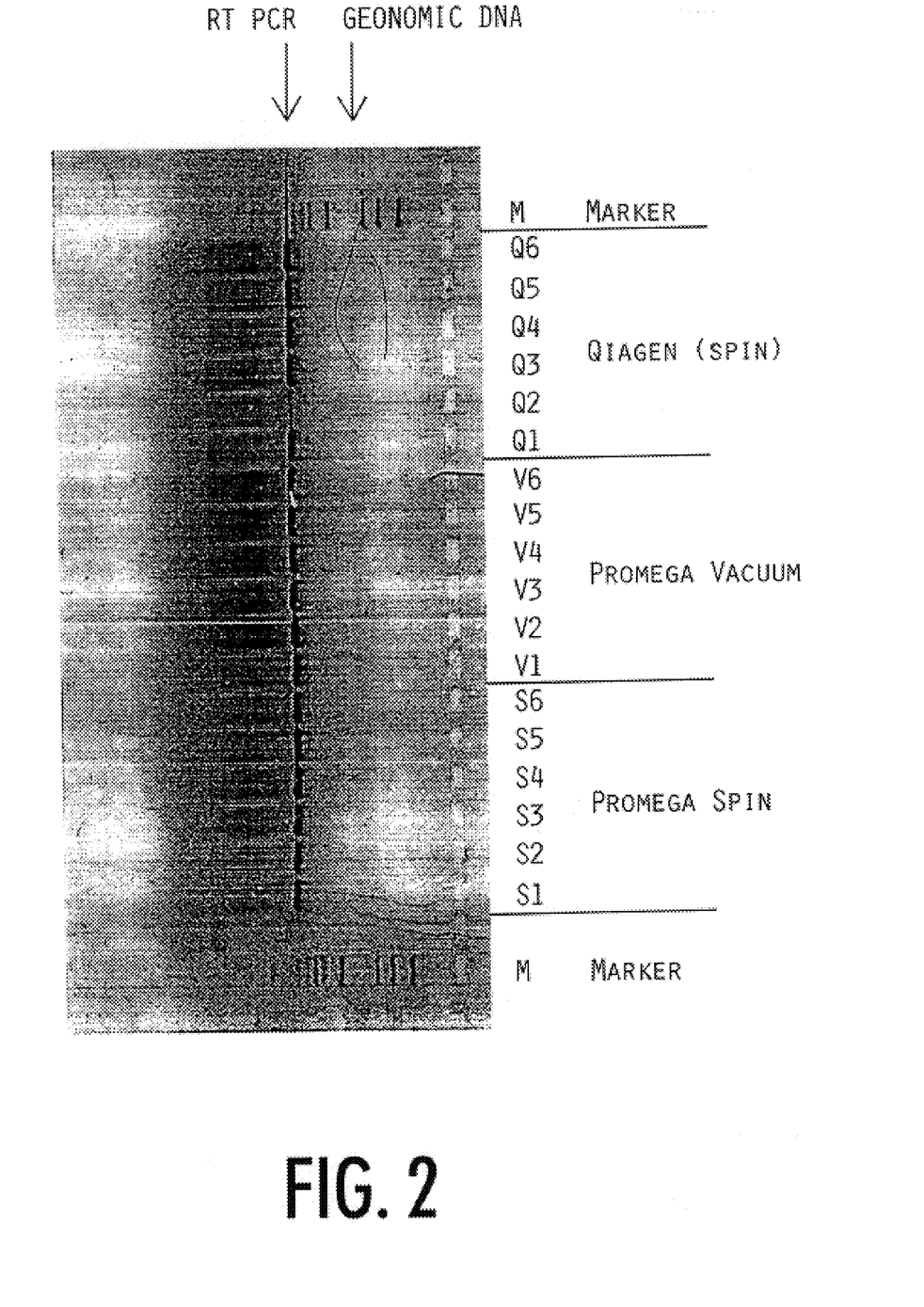
FIG. 2 is an image of agarose gel electrophoresis of fluorescently labeled reverse transcriptase polymerase chain reaction (RT-PCR) products produced from total RNA isolated from mouse liver tissue using spin filtration (samples S1–S6) or vacuum filtration (samples V1–V6) with a method of isolation of the present invention and a Wizard® Plus SV Spin Filter from Promega, or using spin filtration with an RNeasy™ Spin Column and the method of isolating RNA with that particular type of spin column disclosed in the RNeasy™ Handbook from QIAGEN (samples Q1–Q6).

FIG. 2 is a fluorimager scan of the agarose gel of electophoresed RT-PCR samples prepared, as described above. The results of the electrophoresis assay clearly demonstrate that RNA isolated according to all three methods, i.e. spin prep using the Wizard® Plus SV Minipreps Spin Column (samples S1–S6), vacuum filtration using the same Spin Column (samples V1–V6), and spin prep using the QIAGEN Spin Column and procedure, produced intact DNA when processed with RT-PCR. However, the gel also shows that RNA isolated with the QIAGEN column and procedures contained significant chromosomal DNA contamination, as evidenced by the large molecular weight bands marked by an arrow in FIG. 2.

What is claimed is:
1. A method of isolating RNA from a biological material, comprising the steps of
   a) providing a biological material comprising RNA and contaminants, wherein the contaminants include DNA and proteins;
   b) disrupting the biological material in a first container in the presence of a lysis buffer containing a chaotropic salt, thereby producing a lysate solution and cell debris, wherein the concentration of chaotropic salt in the lysis buffer is at least about 0.5 molar;
   c) adding a sufficient volume of a dilution buffer to the lysate solution to form a precipitate of the contaminants in the lysate solution; and
   d) removing the precipitate from the diluted lysate solution, thereby forming a cleared lysate solution.
2. The method of isolating RNA of claim 1, wherein the biological material disrupted in step (b) is in the presence of a lysis buffer containing a guanidinium salt chaotropic salt.
3. The method of isolating RNA of claim 1, wherein the biological material is disrupted in step (b) in the presence of a lysis buffer further containing a detergent and a buffer, wherein the pH of the lysis buffer is at least 6 and up to 8.5.
4. The method of isolating RNA of claim 1, wherein the lysate solution is diluted in step (c) with a dilution buffer, wherein the dilution buffer comprises water, a salt, and a buffer.
5. The method of isolating RNA of claim 4, wherein the lysate solution is diluted in step (c) with a dilution buffer, wherein the dilution buffer further comprises a detergent.
6. The method of isolating RNA of claim 1, wherein the precipitate and cell debris are removed from the diluted lysate in step (d) by centrifuging the diluted lysate in a first container, and by transferring the resulting cleared lysate solution into a second container.
7. The method of isolating RNA of claim 1, further comprising the steps of:
   e) providing a silica matrix with a capacity to bind RNA;
   f) adding a reagent mixture to the decanted diluted lysate, thereby forming a binding mixture, wherein the reagent mixture is configured to promote binding of the RNA to a silica matrix;
   g) placing the binding mixture in contact with the silica matrix, wherein the RNA forms a complex with the silica matrix;
   h) removing the binding mixture from the complex;
   i) washing the complex by adding at least one wash solution to the complex and removing it therefrom;
   j) eluting the RNA from the complex by placing the complex into contact with an elution buffer, thereby promoting release of the RNA from the complex into the elution buffer; and
   k) removing the elution buffer containing the eluted RNA from the complex.
8. The method of isolating RNA of claim 7, wherein the silica matrix provided in step (e) is in the form of a filter basket configured to fit into a centrifuge tube.
9. The method of isolating RNA of claim 8, wherein the binding mixture is removed in step (h) and the wash solution is removed in step (i) by placing the filter basket into a centrifuge tube and centrifuging the resulting centrifuge tube/filter assembly.
10. The method of isolating RNA of claim 8, wherein the silica matrix provided in step (e) is in the form of a filter basket which is further configured to fit a vacuum adapter and to be mounted on a vacuum manifold through the adapter, and wherein the binding mixture is removed in step (h) and the wash solution is removed in step (i) by vacuum filtration using the vacuum adapter and vacuum manifold.

11. The method of isolating RNA of claim 7, wherein the reagent mixture added to the diluted lysate solution in step (f) contains at least one binding enhancer selected from the group consisting of sodium chloride, n alcohol, and a chaotropic salt.

12. The method of isolating RNA of claim 7, wherein the RNA/matrix complex is washed in step (i) with a wash solution, wherein the wash solution comprises a buffer and at least 30% by volume of an alcohol.

13. The method of isolating RNA of claim 7, wherein the RNA is eluted from the RNA/matrix complex using an elution buffer, wherein the elution buffer is selected from the group consisting of water and TE buffer.

14. The method of isolating RNA of claim 7, wherein the binding mixture formed in step (f) further comprises DNA, and wherein the complex of RNA and the silica matrix formed when the binding mixture is placed in contact with the silica matrix in step (g) further comprises RNA, wherein the DNA is removed from the complex by digestion with DNase before the RNA is eluted from the complex in step (j).

15. The method of isolating RNA of claim 14, wherein the DNA is removed from the complex by digestion with DNase after washing the complex according to step (i) and before eluting the RNA from the complex according to step (j), according to the additional steps comprising:

placing the complex in contact with DNase in the presence of a DNase incubation buffer;

incubating the DNase and complex mixture for at least one minute to allow the DNase to digest the DNA;

adding a chaotropic salt mixture to the complex at the end of the incubation period, wherein the chaotropic salt mixture comprises a sufficient amount of a chaotropic salt to inactivate the DNase and to promote retention of RNA in the complex;

removing the chaotropic salt mixture from the complex; and washing the complex again according to washing step (j).

16. The method of isolating RNA of claim 15, wherein the complex is placed into contact with DNase in the presence of a DNase incubation buffer, wherein the incubation buffer is buffered to a pH of at least 7 and up to 9, and wherein the incubation buffer contains at least about 1 mM magnesium chloride and up to about 1 M sodium chloride.

* * * * *